US012599781B2

(12) United States Patent
Petaja et al.

(10) Patent No.: US 12,599,781 B2
(45) Date of Patent: Apr. 14, 2026

(54) ASSESSING TREATMENT PARAMETERS FOR RADIATION TREATMENT PLANNING

(71) Applicant: Siemens Healthineers International, Steinhausen (CH)

(72) Inventors: Viljo Petaja, Espoo (FI); Anthony Magliari, Swansea, IL (US); Pierre Lansonneur, Helsinki (FI); Jessica Perez, Geneva (CH); Michiko Rossi, Espoo (FI); Michael Folkerts, Carrollton, TX (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

(21) Appl. No.: 18/108,539

(22) Filed: Feb. 10, 2023

(65) Prior Publication Data
US 2023/0191153 A1 Jun. 22, 2023

Related U.S. Application Data

(62) Division of application No. 17/362,694, filed on Jun. 29, 2021, now Pat. No. 11,590,363.

(51) Int. Cl.
*A61N 5/00* (2006.01)
*A61N 5/10* (2006.01)

(52) U.S. Cl.
CPC ......... *A61N 5/1031* (2013.01); *A61N 5/1045* (2013.01); *A61N 5/1048* (2013.01); *A61N 2005/1074* (2013.01)

(58) Field of Classification Search
None
See application file for complete search history.

(56) References Cited

U.S. PATENT DOCUMENTS

| | | | | |
|---|---|---|---|---|
| 2003/0111612 A1* | 6/2003 | Lightfoot | ............... | G01T 1/169 250/394 |
| 2013/0102830 A1 | 4/2013 | Otto | | |
| 2013/0197878 A1 | 8/2013 | Fiege et al. | | |
| 2018/0185669 A1* | 7/2018 | Kuusela | .............. | A61N 5/1031 |
| 2019/0054320 A1 | 2/2019 | Owens et al. | | |
| 2020/0282233 A1 | 9/2020 | Folkerts et al. | | |
| 2020/0286601 A1* | 9/2020 | Khuntia | ................. | G16H 15/00 |
| 2021/0052916 A1* | 2/2021 | Isola | .................... | A61N 5/1048 |
| 2021/0361253 A1* | 11/2021 | Griffiths | ................. | G16H 20/40 |

FOREIGN PATENT DOCUMENTS

| | | | |
|---|---|---|---|
| EP | 3264298 A1 | 1/2018 | |
| WO | WO-2021/259977 A1 | 12/2021 | |

* cited by examiner

*Primary Examiner* — Hoon K Song

(74) *Attorney, Agent, or Firm* — Harness, Dickey & Pierce, P.L.C.

(57) ABSTRACT

Information associated with a radiation treatment plan includes, for example, values of dose per voxel in a target volume, values of dose rate per voxel in the target volume, and values of parameters used when generating the values of dose per voxel and the values of dose rate per voxel. Renderings that include, for example, a rendering of an image of or including the target volume, and a rendering of selected values of the radiation treatment plan, are displayed. When a selection of a region of one of the renderings is received, a displayed characteristic of another one of the renderings is changed based on the selection.

16 Claims, 8 Drawing Sheets

100

PATIENT-
SPECIFIC
INFORMATION
201

200

210
INPUT
INTERFACE

150
OPTIMIZER
MODEL

220
DATA
PROCESSING

230
OUTPUT
INTERFACE

PREDICTION

TREATMENT
PLAN BASED
ON THE
PREDICTION

300

400

1100

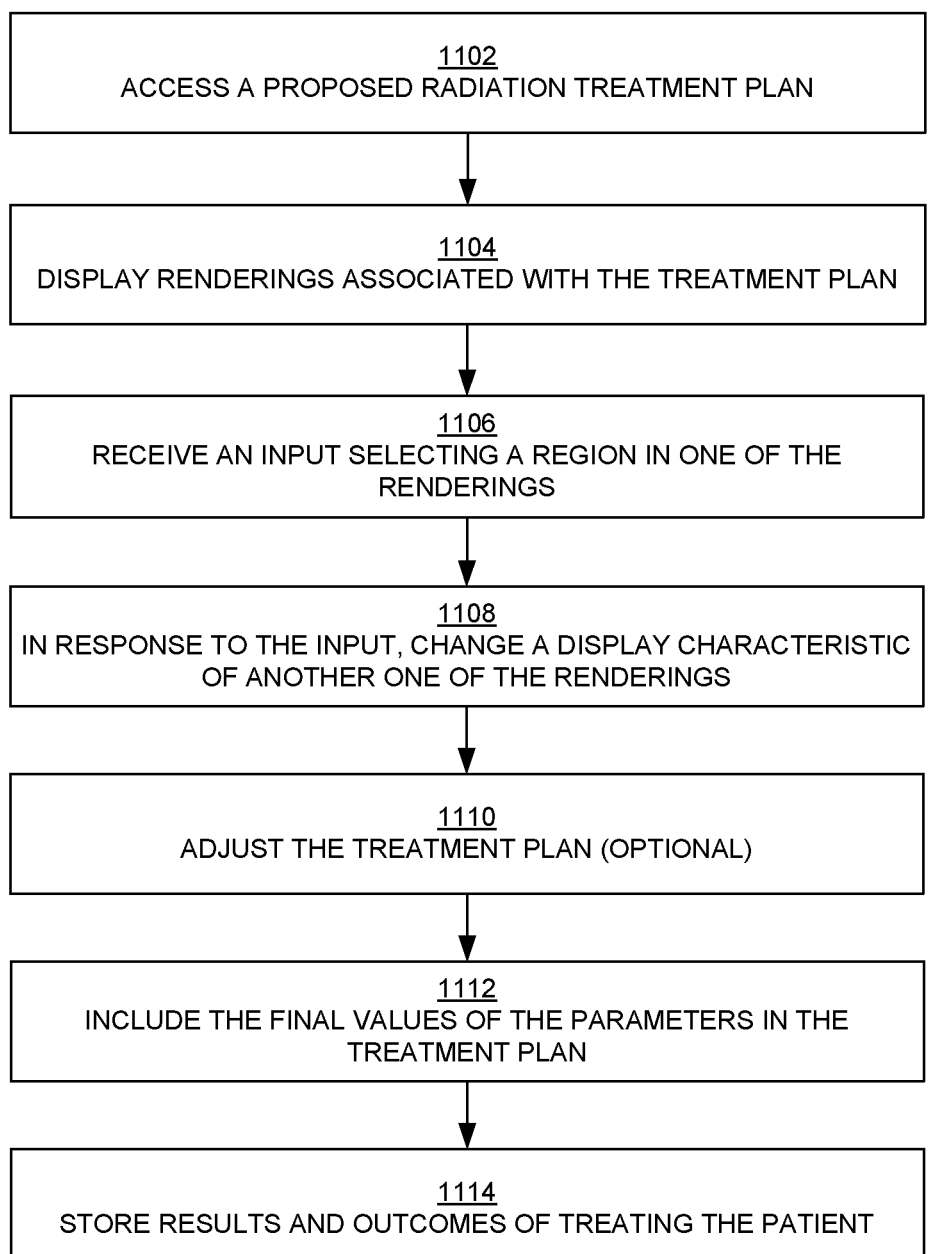

1102
ACCESS A PROPOSED RADIATION TREATMENT PLAN

1104
DISPLAY RENDERINGS ASSOCIATED WITH THE TREATMENT PLAN

1106
RECEIVE AN INPUT SELECTING A REGION IN ONE OF THE RENDERINGS

1108
IN RESPONSE TO THE INPUT, CHANGE A DISPLAY CHARACTERISTIC OF ANOTHER ONE OF THE RENDERINGS

1110
ADJUST THE TREATMENT PLAN (OPTIONAL)

1112
INCLUDE THE FINAL VALUES OF THE PARAMETERS IN THE TREATMENT PLAN

1114
STORE RESULTS AND OUTCOMES OF TREATING THE PATIENT

Fig. 11

ASSESSING TREATMENT PARAMETERS FOR RADIATION TREATMENT PLANNING

CROSS-REFERENCE TO RELATED APPLICATIONS

This is a continuation of U.S. patent application Ser. No. 17/362,694 filed Jun. 29, 2021, which is incorporated herein in its entirety.

BACKGROUND

The use of radiation therapy to treat cancer is well known. Typically, radiation therapy involves directing a beam of high energy proton, photon, ion, or electron radiation ("therapeutic radiation") into a target or volume in a target volume (e.g., a volume that includes a tumor or lesion).

Before a patient is treated with radiation, a treatment plan specific to that patient is developed. The plan defines various aspects of the therapy using simulations and optimizations that may be based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A radiobiology study has demonstrated the effectiveness of delivering an entire, relatively high therapeutic radiation dose to a target within a single, short period of time. This type of treatment is referred to generally herein as FLASH radiation therapy (FLASH RT). Delivery of the dose can be spatially and/or temporally fractionated. That is, for example, a FLASH treatment of a particular patient can be delivered in multiple fractions, which may be separated in time and/or which may be delivered to different sub-volumes of a target. Evidence to date suggests that FLASH RT advantageously spares normal, healthy tissue from damage when that tissue is exposed to a high radiation dose for only a very short period of time.

FLASH RT introduces important interdependencies that are not captured by conventional radiation treatment planning. Current tools such as dose-volume histograms and dose-rate volume histograms do not capture the interdependence of dose and dose rate. For example, developing a dose rate distribution for a high-quality plan is not trivial from a clinician's perspective because normal tissue might benefit from a low dose rate in certain regions if the dose is minimized in these regions. Also, for example, irradiating a restricted number of spots in a treatment volume may lead to high dose rate delivery but low dose homogeneity at the level of the tumor, while on the other hand, plan quality could be improved by increasing the number of spots at the cost of lowering the dose rate.

SUMMARY

Embodiments according to the present invention provide an improved method of generating and assessing radiation treatment plans for FLASH radiation therapy (FLASH RT).

In embodiments, a computer-implemented method for planning radiation treatment includes accessing, from computer system memory, information associated with a radiation treatment plan. The information includes, for example, values of dose per voxel in a target volume, values of dose rate per voxel in the target volume, and values of parameters used when generating the values of dose per voxel and the values of dose rate per voxel. The values may be pre-treatment values (e.g., values that are generated during treatment planning) or post-treatment values (e.g., values that are generated during and as a result of treatment).

In embodiments, renderings that include, for example, a rendering (which may be referred to as a first rendering) of an image of or including the target volume, and a rendering (which may be referred to as a second rendering) of selected values of the radiation treatment plan, are displayed on a display device of a computer system (e.g., as a graphical user interface, or GUI). When a selection of a region of one of the renderings is received, a displayed characteristic of another one of the renderings is changed based on the selection.

For example, the second rendering may include a dose-dose rate scatter plot, where each point in the scatter plot represents or corresponds to a voxel in the image in the first rendering. A selection of a region in the scatter plot results in the corresponding voxels in the first rendering (image) being highlighted in some manner (e.g., by a change in their color). Conversely, a selection of a region in the image in the first rendering results in the corresponding points in the second rendering being highlighted in some manner (e.g., by a change in their color). Accordingly, dose distribution can be assessed for a range of dose rates, and dose rate distribution can be assessed for a range of doses. Other examples are discussed in the following detailed description.

Embodiments according to the present invention thus provide tools that allow a clinician or treatment planner to readily assess dose distribution and dose rate distribution as well as other parameters as described herein. In essentially a single glance, a clinician can evaluate the quality of a proposed radiation treatment plan, make changes to a proposed plan, and evaluate the results of the changes to produce the highest quality final radiation treatment plan. Similarly, after treatment, a clinician can evaluate results, verify the effects of FLASH RT, correlate outcomes with objectives (clinical goals), and use that information to improve treatment planning in general and subsequent treatment plans in particular.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (target volume) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments according to the invention improve radiation treatment planning and the treatment itself by expanding FLASH RT to a wider variety of treatment platforms and target sites (e.g., tumors). Treatment plans generated as described herein are superior for sparing healthy tissue from radiation in comparison to conventional techniques for FLASH dose rates by optimizing the balance between the dose rate delivered to unhealthy tissue (e.g., a tumor) in a target volume and the dose rate delivered to surrounding healthy tissue. Using FLASH RT, the dose(s) prescribed by a clinician and included in a radiation treatment plan can be fulfilled while maintaining high dose rates (FLASH dose rates). With FLASH dose rates, management of patient motion is simplified because the doses are applied in a short period of time (e.g., less than a second). Treatment planning, while still a complex task, is improved relative to conventional treatment planning. In addition to these benefits, a GUI facilitates treatment planning by allowing a planner to readily visualize key elements of a proposed treatment plan, to readily visualize the effects on those elements of changes to the proposed plan and compare different plans, and to define and establish optimization objectives (clinical goals).

In summary, embodiments according to this disclosure pertain to generating and implementing a treatment plan that is the most effective (relative to other plans) and with the least (or most acceptable) side effects (e.g., a lower dose and higher dose rate outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans, fewer computational resources are needed and consumed, meaning also that computer resources are freed up to perform other tasks.

In addition to radiation therapy techniques such as IMRT and IMPT, embodiments according to the invention can be used in spatially fractionated radiation therapy including high-dose spatially fractionated grid radiation therapy, mini-beam radiation therapy, and microbeam radiation therapy.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

FIG. 11 is a flowchart of an example of computer-implemented operations for radiation treatment planning in embodiments according to the present invention.

DETAILED DESCRIPTION

Figure 1:
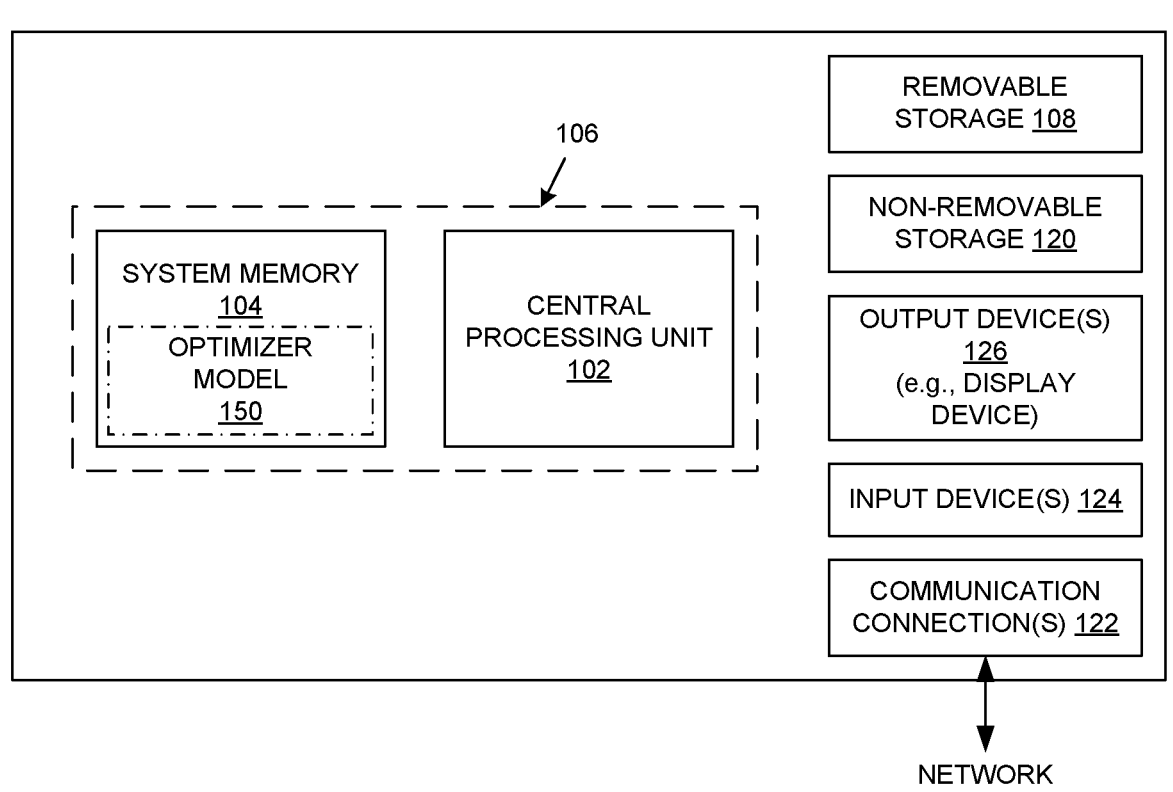
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "generating," "representing," "applying," "indicating," "storing," "using," "adjusting," "including," "computing," "calculating," "determining," "visualizing," "displaying," "rendering," "associating," "changing," or "receiving," "selecting," or the like, refer to actions and processes (e.g., the flowchart of FIG. 11) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow includes terms such as "dose," "dose rate," "energy," etc. Unless otherwise noted, a value is associated with each such term. For example, a dose has a value and can have different values. For simplicity, the term "dose," for example, may refer to a value of a dose, unless otherwise noted or apparent from the discussion.

Portions of the detailed description that follows are presented and discussed in terms of methods. Although steps and sequencing thereof are disclosed in figures herein (e.g., FIG. 11) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included. A display device may be, for example, a cathode ray tube display, a light-emitting diode display, or a liquid crystal display.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
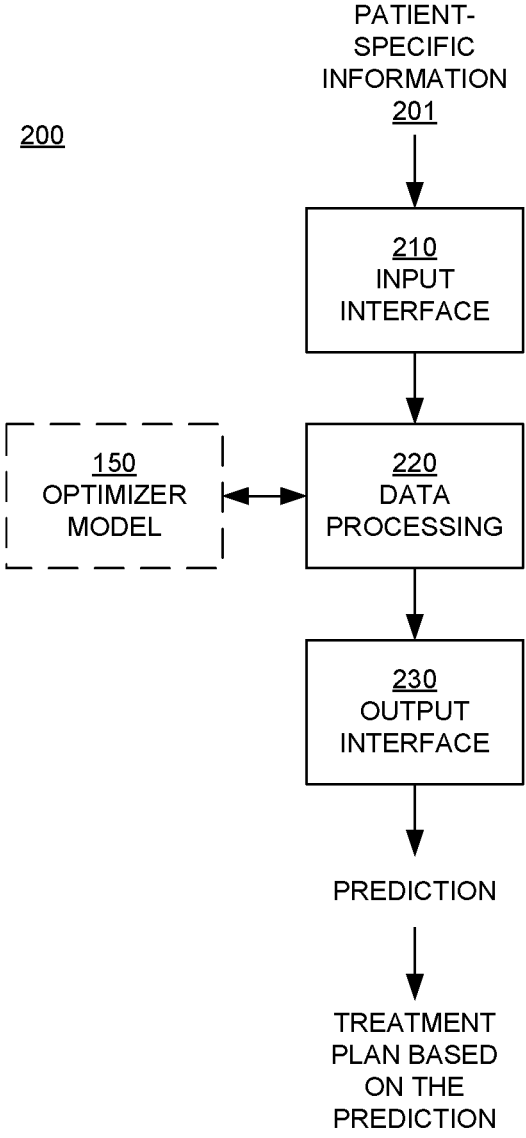
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. In embodiments, the optimizer model 150 yields a prediction result, and a treatment plan based on the prediction result can then be generated.

Figure 3:
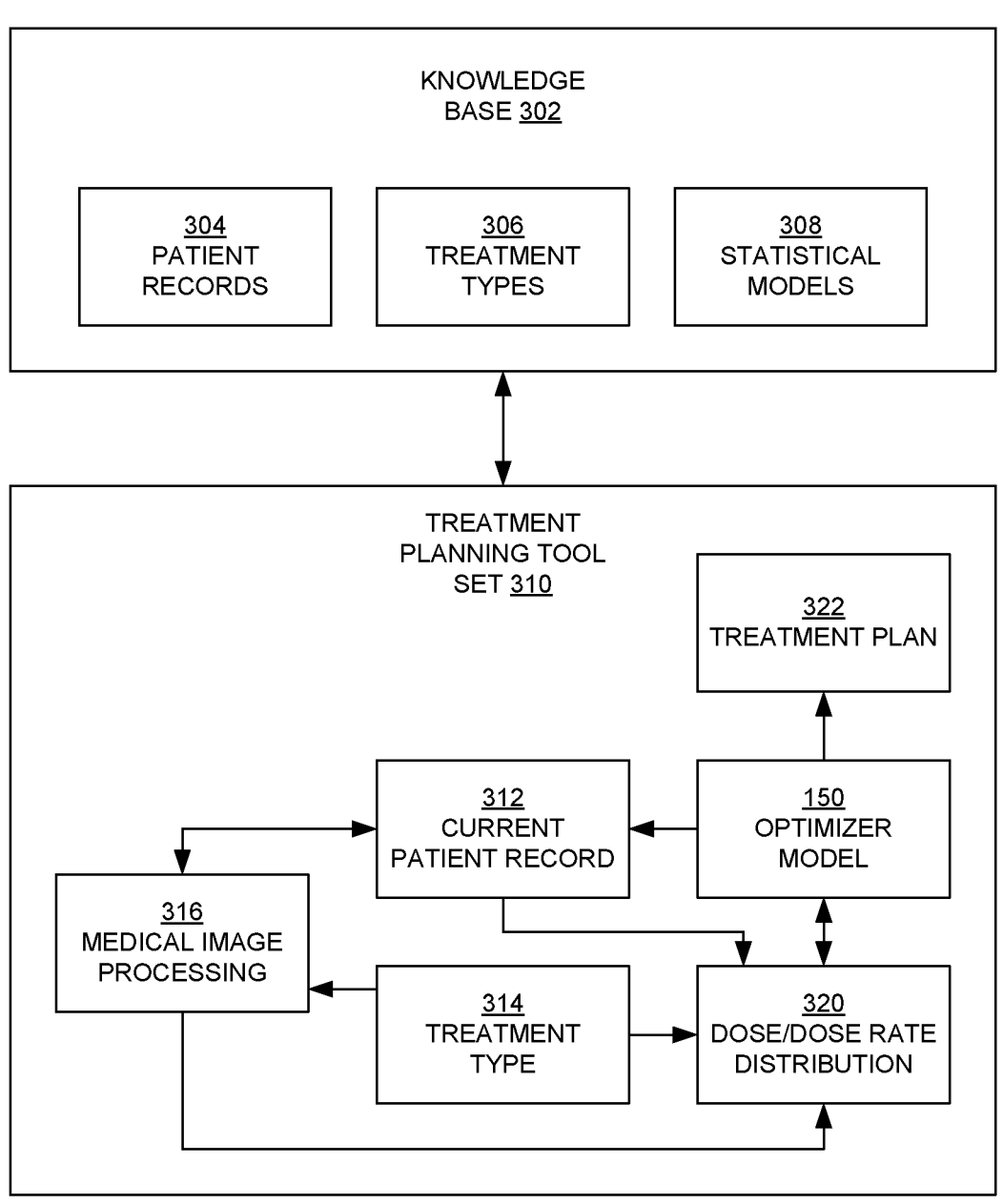
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose and/or dose rate) can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 150.

In embodiments according to the present invention, the optimizer model 150 uses a dose prediction model to provide, for example, a 3D dose distribution, fluences, and dose rates, and associated dose-volume histograms (DVHs) and dose rate-volume histograms (DRVHs).

Figure 4:
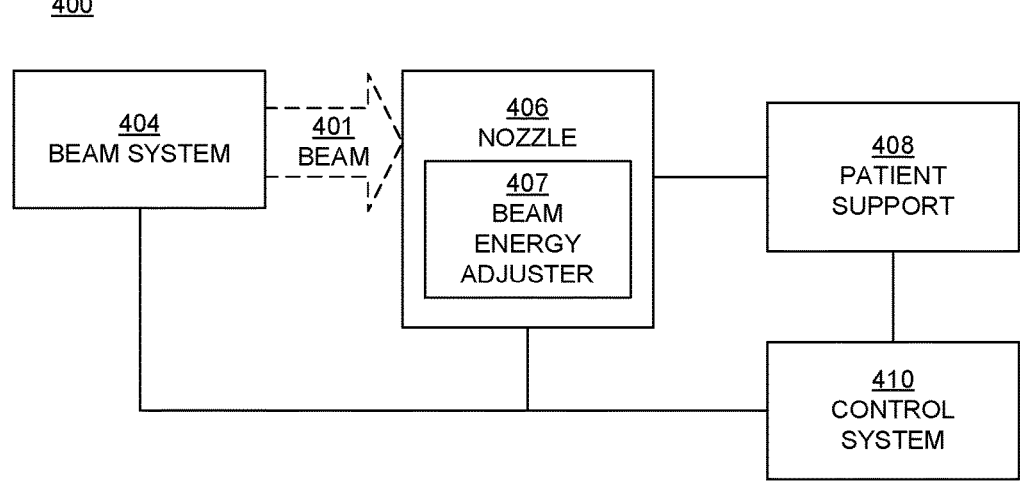
FIG. 4 is a block diagram showing selected components of a radiation therapy system upon which embodiments according to the present invention can be implemented.

FIG. 4 is a block diagram showing selected components of a radiation therapy system 400 upon which embodiments according to the present invention can be implemented. In the example of FIG. 4, the system 400 includes a beam system 404 and a nozzle 406.

The beam system 404 generates and transports a beam 401. The beam 401 can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam system in a direction toward and into a nozzle 406. In embodiments, the radiation therapy system may include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 is used to aim the beam toward various locations (a target volume) (e.g., a volume in a patient) supported on the patient support device 408 (e.g., a chair or table) in a treatment room. A target volume may be an organ (organ-at-risk), a portion of an organ (e.g., a volume or region within the organ), a tumor, diseased tissue, or a patient outline. A target volume may include both unhealthy tissue (e.g., a tumor) and healthy tissue. A target volume may be divided (virtually) into a number of voxels. A sub-volume can include a single voxel or multiple voxels.

The nozzle 406 may be mounted on or a part of a gantry that can be moved relative to the patient support device 408, which may also be moveable. In embodiments, the beam system 404 is also mounted on or is a part of the gantry. In another embodiment, the beam system is separate from (but in communication with) the gantry.

The control system 410 of FIG. 4 receives and implements a prescribed radiation treatment plan. In embodiments, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and/or shape of the beam, according to data it receives and according to the prescribed radiation treatment plan.

As noted above, the beam 401 entering the nozzle 406 has a specified energy. Thus, in embodiments according to the present disclosure, the nozzle 406 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth-dose curve of the beam, depending on the type of beam. For example, for a proton beam or an ion beam that has a Bragg peak, the beam energy adjuster can control the location of the Bragg peak in the target volume. In various embodiments, the beam energy adjuster 407 includes a range modulator, a range shifter, or both a range modulator and a range shifter.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (target volume) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

The beam 401 can have virtually any regular or irregular cross-sectional (e.g., beam's eye view) shape. For example, the shape of the beam 401 can be defined using an MLC that blocks a portion or portions of the beam. Different beams can have different shapes.

In embodiments, the beam 401 includes a number of beam segments or beamlets (that also may be referred to as spots). A maximum energy (e.g., 80 MeV) is specified for the beam 401, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The defined energy level or intensity can be realized for each beam segment using the beam energy adjuster 407.

Each beam segment can deliver a relatively high dose rate (a relatively high dose in a relatively short period of time). For example, each beam segment can deliver at least 40 grays (Gy) in less than one second, and may deliver as much as 120 Gy per second or more.

In operation, in embodiments, the beam segments are delivered sequentially. For example, a first beam segment is delivered to the target volume (turned on) and then turned off, then a second beam segment is turned on then off, and so on. Each beam segment may be turned on for only a fraction of a second (e.g., on the order of milliseconds).

A single beam may be used and applied from different directions and in the same plane or in different planes. Alternatively, multiple beams may be used, in the same plane or in different planes. The directions and/or numbers of beam can be varied over a number of treatment sessions (that is, fractionated in time) so that a uniform dose is delivered across the target volume. The number of beams delivered at any one time depends on the number of gantries or nozzles in the radiation treatment system (e.g., the radiation treatment system 400 of FIG. 4) and on the treatment plan.

Assessing Treatment Parameters for Radiation Treatment Planning

In embodiments according to the present invention, a computer-implemented method for planning and assessing radiation treatment includes accessing, from computer system memory, information associated with a radiation treatment plan. The information includes, for example, values of dose per voxel in a target volume, values of dose rate per voxel in the target volume, and values of parameters used when generating the values of dose per voxel and the values of dose rate per voxel. Renderings that include, for example, a rendering (which may be referred to herein as a first rendering) of an image of or including the target volume, and a rendering (which may be referred to herein as a second rendering) of selected values of the radiation treatment plan, are displayed on a display device of a computer system (e.g., as a graphical user interface, or GUI). When a selection of a region of one of the renderings is received, a displayed characteristic of another one of the renderings is changed based on the selection.

FIGS. 5, 6, 7, 8, 9, and 10 (FIGS. 5-10) illustrate examples of GUIs that can be used to display information associated with radiation treatment planning and assessment in embodiments according to the present invention.

Embodiments according to the present invention are not limited to the GUIs illustrated in FIGS. 5-10. In general, GUIs in embodiments according to the present invention allow the interdependencies between, for example, doses, dose rates, and doses and dose rates per volume (sub-volume or voxel) to be readily visualized for radiation treatment planning and for evaluating treatment outcomes. The doses, dose rates, etc., in the discussion below may be calculated values (calculated during planning using, for example, the optimizer model 150 of FIG. 1) or measured values (measured during and/or after treatment).

The GUIs can be generated as described below (see the discussion of FIG. 11) and implemented using computer-executable instructions residing on some form of computer-readable storage medium (e.g., memory of the computer system 100 of FIG. 1), and can be displayed on the output device (display device) 126 of the computer system.

Also, the disclosed GUIs can include information in addition to that included in the examples. That is, the GUIs can include GUI elements (e.g., other windows or displays) in addition to those described in the examples of FIGS. 5-10. Also, in embodiments, drop-down menus or other types of GUI elements (not shown in the figures) can be used to select and establish settings (e.g., attributes, thresholds, etc.) for the GUIs and the type(s) of information to be displayed at any one time.

Also, the GUIs are not necessarily static displays. For example, the information presented in the GUIs can be programmed to change over time or in response to user inputs to illustrate accumulated dose or dose rate versus time. Also, for example, the GUIs can be programmed to present different cross-sectional slices of the target volume in sequence to provide a depth dimension to a two-dimensional representation, or to manipulate (e.g., rotate) a virtual three-dimensional representation so that it can be viewed from different perspectives.

Figure 5:
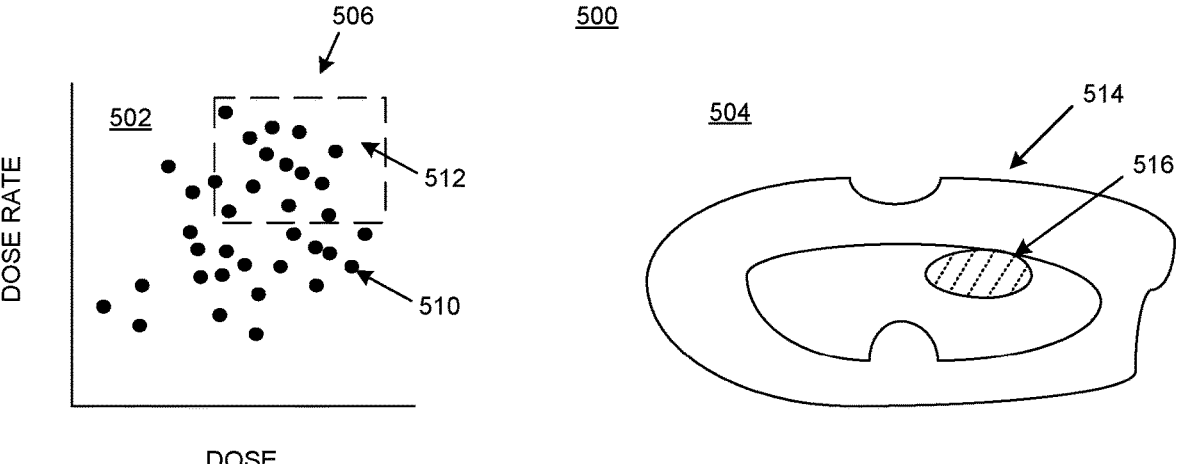
FIG. 5 illustrates an example of a graphical user interface (GUI) that can be used to assess a radiation treatment plan in embodiments according to the present invention.

FIG. 5 illustrates an example of a GUI 500 that can be used to assess a radiation treatment plan in embodiments according to the present invention. In the example of FIG. 5, the GUI 500 includes a first display window or rendering

504 that includes an image 514. The image 514 may be, for example, a cross-sectional view of a volume that includes the target volume. The entire image 514 may be considered as the target volume, or a portion of the image 514 may be considered as the target volume. The target volume may be an organ (organ-at-risk), a portion of an organ (e.g., a volume or region within the organ), a tumor, diseased tissue, or a patient outline.

In this example, the GUI 500 also includes a second display window or rendering 502 that includes a dose-dose rate scatter plot 506. In the scatter plot 506, each point (e.g., the point 510) represents a voxel in the first rendering 504 or image 514.

In an embodiment, the scatter plot 506 may include only the voxels that satisfy a user-defined requirement. For example, the scatter plot 506 may only include voxels that are irradiated by more than a threshold number of (e.g., three) fields or beams.

A selection of a region of interest (e.g., the region 512) in the scatter plot 506 results in the corresponding voxels (e.g., the region 516) in the first rendering 504 being highlighted in some manner (e.g., by a change in color or color shade, pattern, degree of gray-scale, alphanumeric text, or brightness). Conversely, a selection of a region of interest (e.g., the region 516) in the image 514 in the first rendering 504 results in the corresponding points (e.g., the region 512) in the second rendering 502 being highlighted in some manner (e.g., by a change in color or color shade, pattern, degree of gray-scale, alphanumeric text, or brightness).

Accordingly, dose distribution can be assessed for a range of dose rates, and dose rate distribution can be assessed for a range of doses. For FLASH RT, a high dose and high dose rate are desirable. Accordingly, for example, a user can select a region of interest in the scatter plot 506 (e.g., the high dose and high dose rate region), and can visualize the voxels from that region overlaid on the target volume image, such that the user can inspect the precise locations of voxels with different dose-dose rate characteristics.

The regions 512 and 516 can include any number of (one or more) voxels. The selections of the region 512 and the region 516 can be made using any type of selection tool (a rectangle, a lasso, etc.).

Figure 6:
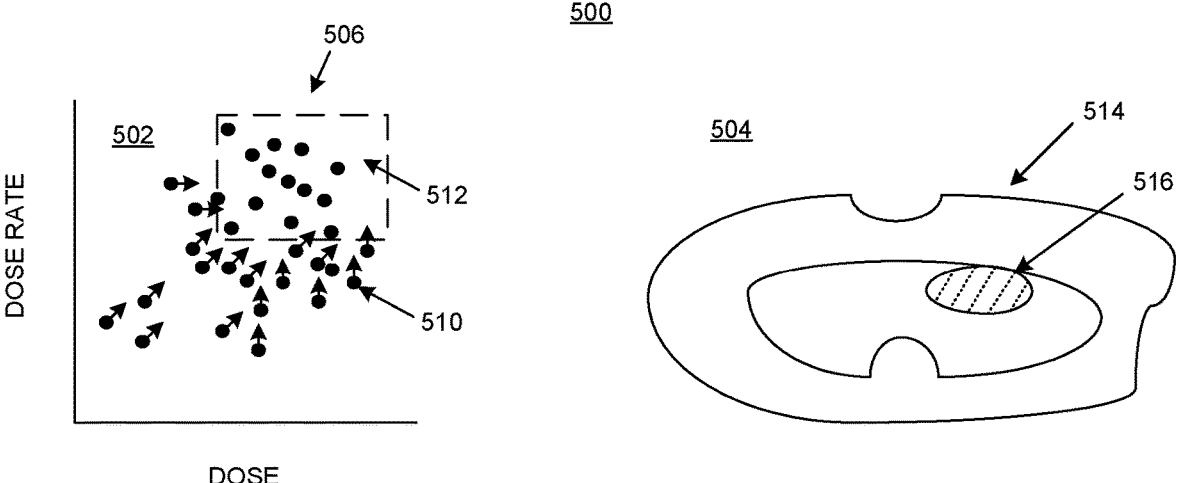
FIG. 6 illustrates an example of how a GUI can be used to improve or optimize a radiation treatment plan in embodiments according to the present invention.

FIG. 6 illustrates an example of how the GUI 500 can be used to improve or optimize a radiation treatment plan in embodiments according to the present invention. As discussed above, a region of interest (e.g., the region 516) can be selected in the first rendering 504. For example, the region 516 may be a contour of a tumor that is to be treated. In response to the selection, voxels corresponding to the region 516 are highlighted in the second rendering 502 or scatter plot 506. For FLASH RT, a high dose and high dose rate are desirable, but some of the voxels corresponding to the region 516 may not be within the high dose-high dose rate region (e.g., they may be outside the region 512).

Using the scatter plot 506 in the second rendering 502, a treatment goal can be set. The treatment goal may be to have all (or at least a threshold number) of the voxels corresponding to the region 516 be within the region 512. The values of the parameters in the treatment plan can be changed, and the modified plan can be evaluated using the optimizer model 150 of FIG. 1. The dose per voxel and the dose rate per voxel that are calculated based on the modified plan are then displayed in the second rendering 502, and a clinician can readily visualize whether the modified plan satisfies the treatment goal. That is, using the GUI 500, a clinician can readily visualize whether, based on the modified plan, all or the threshold number of voxels corresponding to the region 516 are within the region 512.

The points in the scatter plot 506 can also be used to form or define structures or contours in the image 514. Dose rate improvement and optimization objectives can then be assigned to those structures or contours, to improve the quality of the treatment plan.

Figure 7:
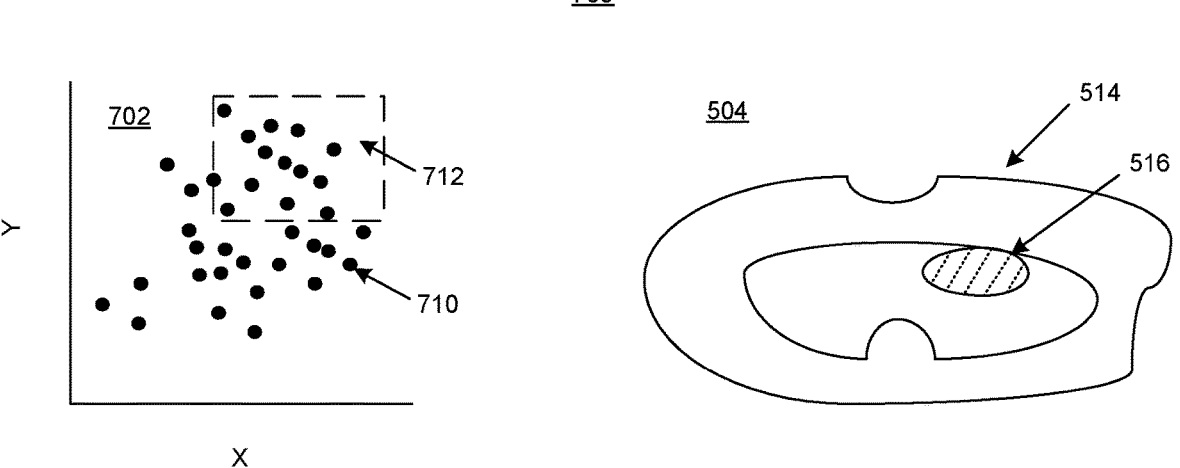
FIGS. 7, 8, 9, and 10 illustrate examples of GUIs that can be used to assess a radiation treatment plan in embodiments according to the present invention.

FIG. 7 illustrates an example of a GUI 700 that can be used to assess a radiation treatment plan in embodiments according to the present invention. In the example of FIG. 7, the GUI 700 includes the first rendering 504 that includes the image 514 as described above. In this example, the GUI 700 also includes a second display window or rendering 702 that illustrates, in two dimensions (x and y), where beams (beam segments or beamlets) intersect the target volume. In the second rendering 702, each point (e.g., the point 710) represents a location or spot in the first rendering 504 or image 514 that is intersected by a beam segment.

The spots in the second rendering 702 can be for a given beam segment or field in the beams-eye view. The spots may be filtered in some way. For example, the spots that are rendered can be for those beam segments or fields that contribute more than a threshold amount of dose and/or more than a threshold amount of dose rate to the target volume. For example, the second rendering 702 may only include spots for the beam segments or fields that contribute more than 0.1 Gy to the target volume.

A set of the spots (e.g., the set 712) can be selected, and corresponding voxels in the first rendering 504 or image 514 are then highlighted in some manner. The highlighted voxels correspond to the locations of the selected spots or to a region of influence affected by the beamlets corresponding to those spots. Conversely, a selection of a region of interest (e.g., the region 516) in the image 514 in the first rendering 504 results in the corresponding spots (e.g., the set 712) in the second rendering 702 being highlighted in some manner.

Figure 8:
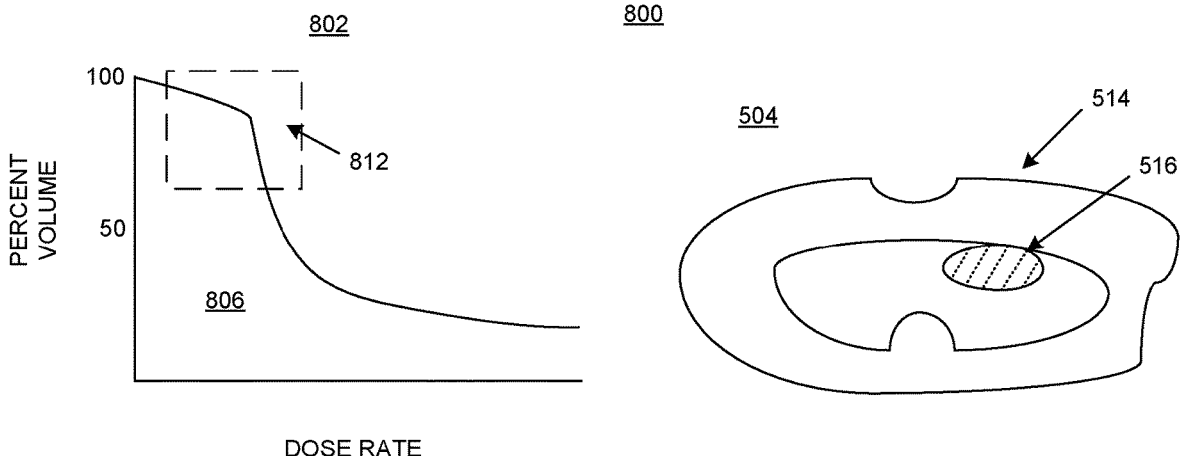

FIG. 8 illustrates an example of a GUI 800 that can be used to assess a radiation treatment plan in embodiments according to the present invention. In the example of FIG. 8, the GUI 800 includes the first rendering 504 that includes the image 514 as described above. In this example, the GUI 800 also includes a second display window or rendering 802 that includes a DRVH 806. A selection of a region of interest (e.g., the region 812) in the DRVH 806 results in the corresponding voxels (e.g., the region 516) in the first rendering 504 being highlighted in some manner. Conversely, a selection of a region of interest (e.g., the region 516) in the image 514 in the first rendering 504 results in the corresponding portion (e.g., the region 812) of the DRVH 806 being highlighted in some manner.

Figure 9:
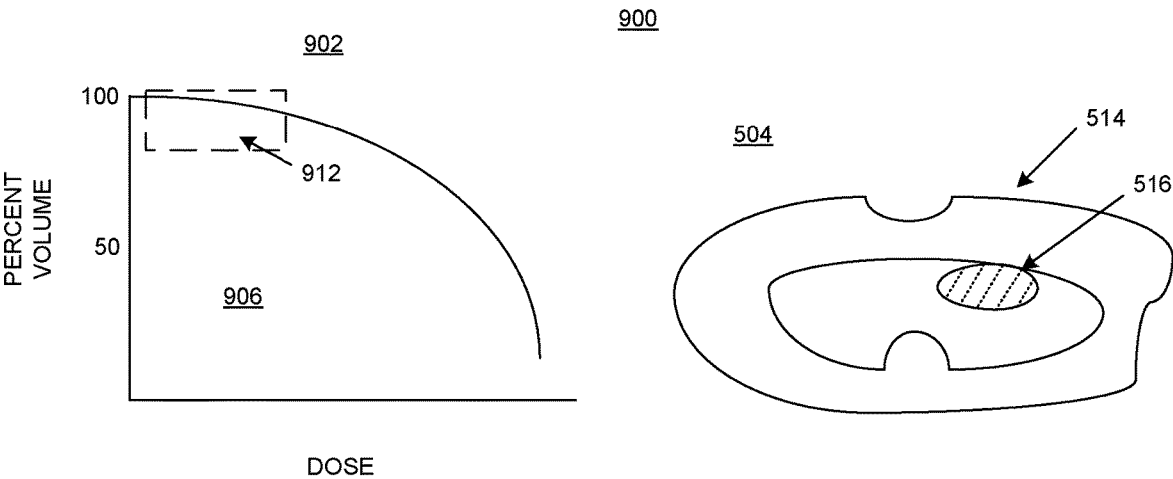

FIG. 9 illustrates an example of a GUI 900 that can be used to assess a radiation treatment plan in embodiments according to the present invention. In the example of FIG. 9, the GUI 900 includes the first rendering 504 that includes the image 514 as described above. In this example, the GUI 900 also includes a second display window or rendering 902 that includes a DVH 906. A selection of a region of interest (e.g., the region 912) in the DVH 906 results in the corresponding voxels (e.g., the region 516) in the first rendering 504 being highlighted in some manner. Conversely, a selection of a region of interest (e.g., the region 516) in the image 514 in the first rendering 504 results in the corresponding portion (e.g., the region 912) of the DVH 906 being highlighted in some manner.

Figure 10:
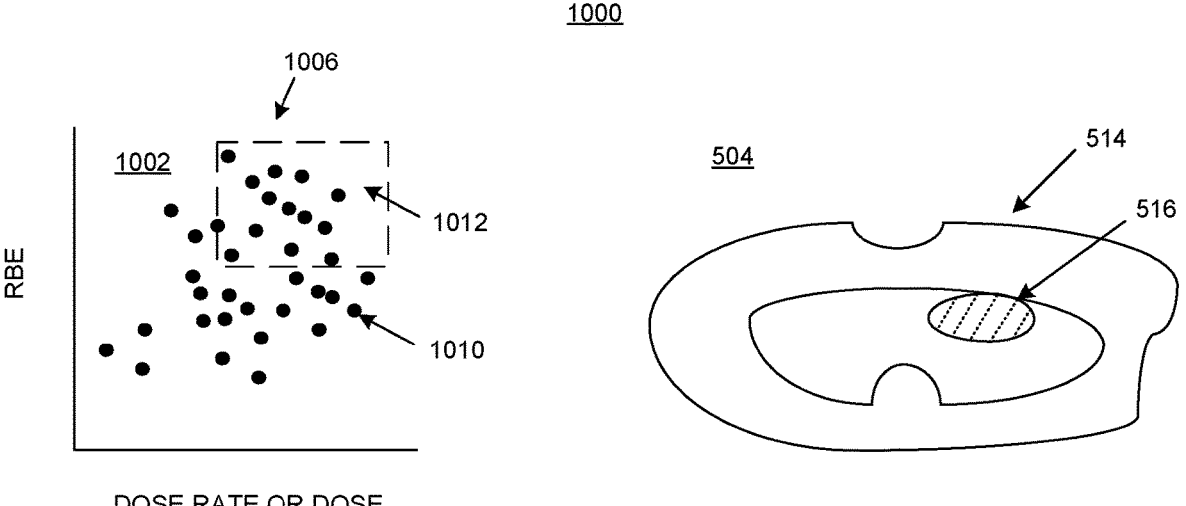

FIG. 10 illustrates an example of a GUI 1000 that can be used to assess a radiation treatment plan in embodiments according to the present invention. In the example of FIG.

10, the GUI 1000 includes the first rendering 504 that includes the image 514 as described above. In this example, the GUI 1000 also includes a second display window or rendering 1002 that illustrates a scatter plot 1006 of relative biological effectiveness (RBE) and dose rate or dose. Markers or measures other than RBE can be used. In the second rendering 1002, each point (e.g., the point 1010) in the scatter plot 1006 represents a voxel in the first rendering 504 or image 514.

A selection of a region of interest (e.g., the region 1012) in the scatter plot 1006 results in the corresponding voxels (e.g., the region 516) in the first rendering 504 being highlighted in some manner. Conversely, a selection of a region of interest (e.g., the region 516) in the image 514 in the first rendering 504 results in the corresponding points (e.g., the region 1012) in the second rendering 1002 or scatter plot 1006 being highlighted in some manner.

The information in the GUIs of FIGS. 5-10 can be used for studying the outcomes of radiation treatment, and for evaluating FLASH RT in particular. For example, the image 514 may be acquired post-treatment, and structures, organs, or contours in the image can be mapped to points in the scatter plots described above. If, for example, fibrosis is detected in a region of the image 514, then that region can be selected and the corresponding voxels in the respective scatter plots will be highlighted, allowing a researcher or clinician to correlate the fibrosis to dose, dose rate, and/or RBE. In general, outcomes can be readily correlated to treatment objectives (clinical goals) and the values of parameters in the treatment plan, and that information can be used to improve treatment planning and to verify the efficacy of FLASH RT, for example.

FIG. 11 is a flowchart 1100 of an example of computer-implemented operations for radiation treatment planning in embodiments according to the present invention. The flowchart 1100 can be implemented as computer-executable instructions (e.g., the optimizer model 150 of FIG. 1) residing on some form of computer-readable storage medium (e.g., in memory of the computer system 100 of FIG. 1).

In block 1102 of FIG. 11, a proposed radiation treatment plan is defined (e.g., using the optimizer model 150 of FIGS. 1 and 2), stored in a computer system memory, and accessed from that memory. The proposed radiation treatment plan identifies a target volume, and includes values of dose per voxel in the target volume, and values of dose rate per voxel in the target volume. The proposed radiation treatment plan includes values of parameters that can affect and/or are used to calculate or generate values of dose and dose rate, as well as values of other parameters. The parameters that can affect dose and dose rate include, but are not limited to, a number of irradiations of the target volume, a duration of each of the irradiations (irradiation times), and a dose deposited in each of the irradiations. The parameters may also include directions of beams (beamlets) to be directed into the target volume, the locations (spots) in the target volume where each beam (beamlet) intersects the target volume, and energies for each of the beams/beamlets. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). If the target volume is divided into sub-volumes or voxels, then the values of the parameters can be on a per-sub-volume or per-voxel basis (e.g., a value per sub-volume or per voxel).

Appropriate dose threshold curve(s) (e.g., normal tissue sparing dose versus dose rate or irradiation time) can be utilized in the optimization model 150 (FIG. 3) to establish dose limits for radiation treatment planning. For example, the appropriate (e.g., tissue-dependent) dose threshold curve can be used to determine beam directions (gantry angles) and beam segment weights. That is, parameters that affect dose can be adjusted during radiation treatment planning so that the limits in the dose threshold curve are satisfied. The dose threshold curves can be tissue-dependent. For instance, the dose threshold curve for the lungs may be different from that for the brain.

Dose limits can include, but are not limited to: a maximum limit on irradiation time for each sub-volume (voxel) in the target (e.g., for each voxel of target tissue, treatment time less than x1 seconds); a maximum limit on irradiation time for each sub-volume (voxel) outside the target (e.g., for each voxel of normal tissue, treatment time less than x2 seconds; x1 and x2 may be the same or different); a minimum limit on dose rate for each sub-volume (voxel) in the target (e.g., for each voxel of target tissue, dose rate greater than y1 Gy/sec); and a minimum limit on dose rate for each sub-volume (voxel) outside the target (e.g., for each voxel of normal tissue, dose rate greater than y2 Gy/sec; y1 and y2 may be the same or different). In general, the limits are intended to minimize the amount of time that normal tissue is irradiated.

In block 1104 of FIG. 11, in an embodiment, renderings are displayed on an output device (e.g., the display device 126 of FIG. 1). The renderings can include, but are not limited to, a rendering of an image that includes the target volume, and a rendering of selected values, as described in the examples of FIGS. 5-10.

In block 1106 of FIG. 11, in an embodiment, an input is received, where the input includes a selection of a region in one of the renderings, as described in the examples of FIGS. 5-10.

In block 1108 of FIG. 11, in an embodiment, in response to receiving the input, a displayed characteristic of another one of the renderings is changed based on the selection, as described in the examples of FIGS. 5-10.

In block 1110 of FIG. 11, some or all of the parameter values for the proposed radiation treatment plan can be iteratively adjusted optionally or if necessary, to determine a final set of parameter values that results in a prescribed (final) radiation treatment plan that best satisfies the objectives (clinical goals) for treatment of the patient.

In block 1112, the final set of parameter values is then included in the prescribed radiation treatment plan used to treat the patient.

In block 1114, the patient is treated according to the prescribed radiation treatment plan, and results and outcomes are generated and stored for subsequent evaluation as mentioned above.

While the operations in FIG. 11 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

In summary, embodiments according to the invention improve radiation treatment planning and the treatment itself by expanding FLASH RT to a wider variety of treatment platforms and target sites. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. Using FLASH RT, the doses prescribed by a clinician and included in a radiation treatment plan are fulfilled while maintaining high dose rates (FLASH dose rates). With FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to those benefits, a GUI facilitates treatment planning by allowing a planner to readily visualize key elements of a treatment plan (e.g., the dose rate per voxel), to readily visualize the effects on those elements of changes to the plan, and to readily visualize a comparison between different plans.

In addition to radiation therapy techniques in which the intensity of the particle beam is either constant or modulated across the field of delivery, such as IMRT and IMPT, embodiments according to the invention can be used in spatially fractionated radiation therapy including high-dose spatially fractionated grid radiation therapy, minibeam radiation therapy, and microbeam radiation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. One or more non-transitory computer-readable storage medium storing computer-executable instruction that, when executed by a computer system, cause the computer system to perform a radiation treatment planning method comprising:

displaying, on a display device of the computer system, a first rendering and a second rendering, wherein the first rendering includes an image of a target volume using a first display characteristic, and wherein the second rendering represents at least a portion of the target volume and includes parameter values of a radiation treatment plan for the target volume using a second display characteristic; and in response to receiving an input including a selection of a sub-region of a given one of the first rendering or the second rendering, changing the given one of the first display characteristic or the second display characteristic of a corresponding sub-region of another one of the first rendering or the second rendering, wherein the second rendering includes a rendering showing locations in the target volume intersected by a given beam segment or field in a beams-eye view.

2. The one or more non-transitory computer-readable storage medium storing computer-executable instruction that, when executed by the computer system, cause the computer system to perform the radiation treatment planning method according to claim 1, wherein the locations in the second rendering are locations where the given beam segment or field delivers more than a threshold amount of dose.

3. The one or more non-transitory computer-readable storage medium storing computer-executable instruction that, when executed by the computer system, cause the computer system to perform the radiation treatment planning method according to claim 1, wherein the locations in the second rendering are locations where the given beam segment or field delivers more than a threshold dose rate.

4. The one or more non-transitory computer-readable storage medium storing computer-executable instruction that, when executed by the computer system, cause the computer system to perform the radiation treatment planning method according to claim 1, wherein the parameter values of the radiation treatment plan include one or more of dose per voxel in a target volume, dose rate per voxel in the target volume, or relative biological effectiveness (RBE) per voxel.

5. The one or more non-transitory computer-readable storage medium storing computer-executable instruction that, when executed by the computer system, cause the computer system to perform the radiation treatment planning method according to claim 1, wherein the first display characteristic and the second display characteristic are selected from a group including:
color;
pattern;
grayscale;
alphanumeric text; and
brightness.

6. A computer system comprising:
a processor;
a display device coupled to the processor; and
a memory coupled to the processor, the memory storing instructions that, when executed by the processor, cause the computer system to:
display, on the display device of the computer system, a first rendering and a second rendering, wherein the first rendering includes an image of a target volume using a first display characteristic, and wherein the second rendering represents at least a portion of the target volume and includes parameter values of a radiation treatment plan for the target volume using a second display characteristic; and
in response to receiving an input including a selection of a sub-region of a given one of the first rendering or the second rendering, change the given one of the first display characteristic or the second display characteristic of a corresponding sub-region of another one of the first rendering or the second rendering,
wherein the second rendering includes a rendering showing locations in the target volume intersected by a given beam segment or field in a beams-eye view.

7. The computer system of claim 6, wherein the locations in the second rendering are locations where the given beam segments or field delivers more than a threshold amount of dose.

8. The computer system of claim 6, wherein the locations in the second rendering are locations where the given beam segment or field delivers more than a threshold dose rate.

9. The computer system of claim 6, wherein the parameter values of the radiation treatment plan include one or more of dose per voxel in a target volume, dose rate per voxel in the target volume, or relative biological effectiveness (RBE) per voxel.

10. The computer system of claim 6, wherein the first display characteristic and the second display characteristic are selected from a group including:
color;
pattern;
grayscale;
alphanumeric text; and
brightness.

11. One or more non-transitory computer-readable storage medium storing computer-executable instruction that, when executed by a computer system, cause the computer system to perform a radiation treatment planning method comprising:
displaying, on a display device of the computer system, a first rendering and a second rendering, wherein the first rendering includes an image of a target volume using a first display characteristic, and wherein the second rendering represents at least a portion of the target volume and includes parameter values of a radiation treatment plan for the target volume using a second display characteristic; and
in response to receiving an input including a selection of a sub-region of a given one of the first rendering or the second rendering, changing the given one of the first display characteristic or the second display characteristic of a corresponding sub-region of another one of the first rendering or the second rendering,
wherein the second rendering includes a dose-dose rate scatter plot with voxels in the dose-dose rate scatter plot being voxels intersected by more than a threshold number of beams of radiation.

12. The one or more non-transitory computer-readable storage medium storing computer-executable instruction that, when executed by the computer system, cause the computer system to perform the radiation treatment planning method according to claim 11, wherein the parameter values of the radiation treatment plan include one or more of dose per voxel in a target volume, dose rate per voxel in the target volume, or relative biological effectiveness (RBE) per voxel.

13. The one or more non-transitory computer-readable storage medium storing computer-executable instruction that, when executed by the computer system, cause the computer system to perform the radiation treatment planning method according to claim 11, wherein the first display characteristic and the second display characteristic are selected from a group including:
color;
pattern;
grayscale;
alphanumeric text; and
brightness.

14. A computer system comprising:
a processor;
a display device coupled to the processor; and
a memory coupled to the processor, the memory storing instructions that, when executed by the processor, cause the computer system to
display, on the display device, a first rendering and a second rendering, wherein the first rendering includes an image of a target volume using a first display characteristic, and wherein the second rendering represents at least a portion of the target volume and includes parameter values of a radiation treatment plan for the target volume using a second display characteristic, and in response to receiving an input including a selection of a sub-region of a given one of the first rendering or the second rendering, changing the given one of the first display characteristic or the second display characteristic of a corresponding sub-region of another one of the first rendering or the second rendering, wherein the second rendering includes a dose-dose rate scatter plot with voxels in the dose-dose rate scatter plot being voxels intersected by more than a threshold number of beams of radiation.

15. The computer system of claim 14, wherein the parameter values of the radiation treatment plan include one or more of dose per voxel in a target volume, dose rate per voxel in the target volume, or relative biological effectiveness (RBE) per voxel.

16. The computer system of claim 14, wherein the first display characteristic and the second display characteristic are selected from a group including:

color;

pattern;

grayscale;

alphanumeric text; and brightness.

* * * * *